(12) United States Patent
Gavaris

(10) Patent No.: US 11,273,073 B2
(45) Date of Patent: Mar. 15, 2022

(54) CANALICULAR PLUG, METHOD AND KIT FOR TREATING DRY EYE

(71) Applicant: Paul Gavaris, Bethesda, MD (US)

(72) Inventor: Paul Gavaris, Bethesda, MD (US)

( * ) Notice: Subject to any disclaimer, the term of this patent is extended or adjusted under 35 U.S.C. 154(b) by 0 days.

(21) Appl. No.: 17/343,066

(22) Filed: Jun. 9, 2021

(65) Prior Publication Data

US 2021/0298956 A1 Sep. 30, 2021

Related U.S. Application Data

(62) Division of application No. 15/536,466, filed as application No. PCT/US2015/006391 on Dec. 4, 2015, now Pat. No. 11,051,982.

(60) Provisional application No. 62/093,271, filed on Dec. 17, 2014.

(51) Int. Cl.
*A61F 9/007* (2006.01)
*A61F 9/00* (2006.01)
*A61F 2/44* (2006.01)

(52) U.S. Cl.
CPC ........ *A61F 9/00772* (2013.01); *A61F 9/0017* (2013.01); *A61F 9/00781* (2013.01); *A61F 2002/4415* (2013.01); *A61F 2230/0069* (2013.01)

(58) Field of Classification Search
CPC .............. A61F 9/00772; A61F 9/00781; A61F 2230/0069; A61F 9/0017; A61F 2002/4415
See application file for complete search history.

(56) References Cited

U.S. PATENT DOCUMENTS

| | | | | |
|---|---|---|---|---|
| 6,428,502 | B1 * | 8/2002 | Lang | A61F 9/00772 604/264 |
| 2002/0198453 | A1 * | 12/2002 | Herrick, II | A61B 17/1204 600/431 |
| 2006/0235367 | A1 * | 10/2006 | Takashima | A61F 9/00781 604/541 |
| 2006/0276738 | A1 | 12/2006 | Becker | A61F 9/00772 604/8 |
| 2009/0240335 | A1 | 9/2009 | Arcenio | A61B 17/7094 623/17.16 |
| 2013/0053794 | A1 * | 2/2013 | Cadden | A61K 9/0092 604/290 |
| 2014/0328894 | A1 | 11/2014 | de Juan, Jr. et al. | |

OTHER PUBLICATIONS

Dr. Simon Barnard. Punctual and intra-canalicular occlusion—a guide for the practioner. Visiting Lecturer, Dept of Optometry & Visual Science, City Unversity, London, Tutorial 1999, p. 1-12.
Shirokova N.V. et al. Osnovy sistrinskogo dela. Algoritmy manipulyatsiy. Uchebnoe posobie dlya mediotsinskikh uchilisch i kolledzhey. M., GEOTAR-Media, 2010, p. 90.

* cited by examiner

*Primary Examiner* — Kai H Weng
(74) *Attorney, Agent, or Firm* — R. Neil Sudol; Henry D. Coleman

(57) ABSTRACT

A plug for occluding an ocular canaliculus comprises a cylindrical body member having a first outer diameter. The cylindrical body member is provided along an external surface with at least one outwardly extending projection having a second outer diameter greater than the first outer diameter and larger than an inner diameter of an ocular canaliculus. The first outer diameter of the plug is typically less than and approximately equal to the inner diameter of the canaliculus.

8 Claims, 2 Drawing Sheets

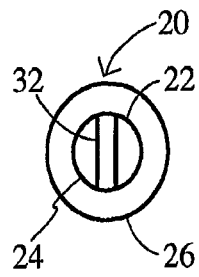
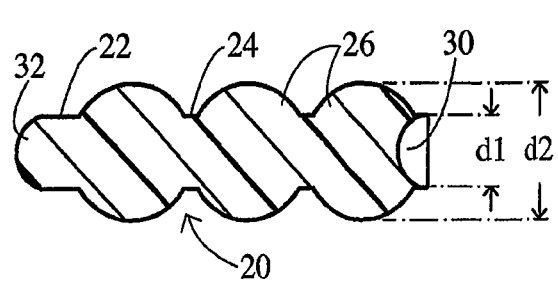
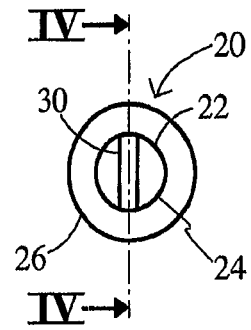
FIG. 3　　　　FIG. 4　　　　FIG. 2
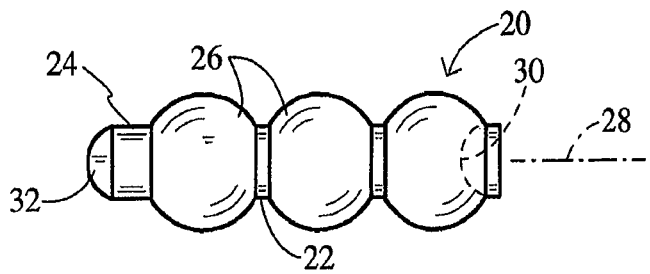
FIG. 1
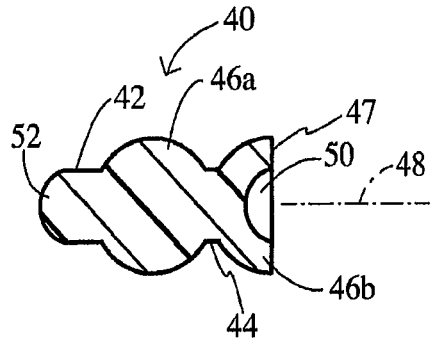
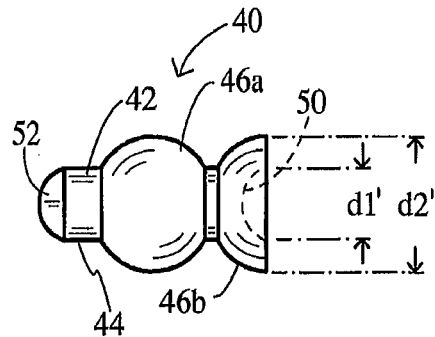
FIG. 6　　　　FIG. 5
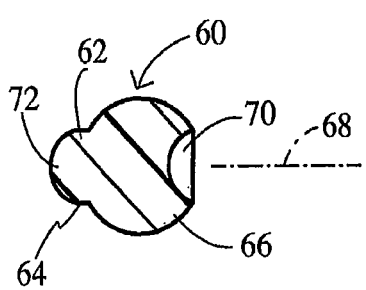
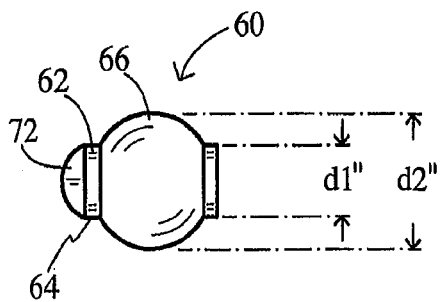
FIG. 8　　　　FIG. 7

CANALICULAR PLUG, METHOD AND KIT FOR TREATING DRY EYE

CROSS-REFERENCE TO RELATED APPLICATIONS

This application is a division of application Ser. No. 15/536,466 filed Jun. 15, 2017 as a U.S. National Stage of International Application No. PCT/US2015/063917 and now issued as U.S. Pat. No. 11,051,982. This application also claims the benefit of U.S. Provisional Patent Application No. 62/093,271 filed Dec. 17, 2014.

BACKGROUND OF THE INVENTION

This invention relates to the treatment of dry eye syndrome. More particularly, this invention relates to a canalicular plug system, a method for treating dry eye syndrome and/or an associated kit.

Keratoconjunctivitis sicca (KCS), also called dry eye syndrome (DES) or keratitis sicca, is an eye disease characterized by eye dryness. Eye dryness arises from either decreased tear production or increased tear film evaporation.

The lacrimal canaliculi, also known as the lacrimal canals, are small channels that commence with tiny openings, termed puncta lacrimalia. There is one canaliculus at each eyelid an upper canaliculus and a lower canaliculus, each having a dog leg shape. Each canaliculus starts at the respective punctum with a short upwardly or downwardly extending segment which communicates with a longer horizontally extending segment that is connected at an inner end to a lacrimal sac.

There are millions of patients with dry eye problems. Many can be helped with plugging of the punctum or canaliculi (all 4 of them). What is not appreciated by many physicians is that plugging of the punctum with external plugs can sometimes increase irritation and dry eye symptoms. Also, a good number of patients, about a third, loose their plugs within the first 3-4 weeks and the plugs have to be replaced. The most important advantage of plugs is that they are visible on examination. To achieve the desired benefit from plugs, i.e., occlusion, one must occlude both upper and lower ducts. However, most of these patients will have epiphora, or spill over from too much tears if the treatment consists of external punctum plugs. It is an all or nothing situation at present.

OBJECTS OF THE INVENTION

It is an object of the present invention to provide an improved method and or apparatus for treating dry eye syndrome.

It is a more particular object of the present invention to provide an improved and effective lacrimal or canalicular plug for insertion into an ocular canaliculus.

Another object of the present invention is to provide a method for customizing the treatment of tear deficient dry eye syndrome with an efficient method of reducing the tear drainage.

A further object of the present invention is to provide a kit that is useful in carrying out the method in a titratable manner.

These and other objects of the present invention will be apparent from the descriptions and drawings herein. Although every object of the invention is attainable by at least one embodiment of the invention, there is not necessarily any single embodiment that achieves all of the objects of the invention.

SUMMARY OF THE INVENTION

A customized tear duct occlusion system as described herein below will afford the physician and patients benefits without the side effects of conventional procedures which can lead to canaliculitis, chronic infections or even dacryocystitis, requiring surgical intervention. Lacrimal or canalicular tear-occluding plugs as described below are indwelling intra canalicular plugs, that is, the plugs are designed for insertion well beyond the punctum and deep into the canaliculi. The plugs are preferably made from a hydrophilic material that thickens sufficiently to block the drainage of tears but also dissipates within 5-6 months' time, using a smart material. The plugs preferably have a corrugated outer surface to help retention and further reduce outflow of tears.

In a customized tear occlusion technique, the upper canaliculus is provided with a plug having a particular diameter and length to fully occlude the upper canaliculus for a specified duration. In the testing or calibration procedure, the lower canaliculus is occluded starting with a half length plug and the patient returns in 2-3 weeks to assess change in tear meniscus or volume and symptoms. Depending on findings, the physician places an additional ¼ sized plug and checks the patient again in 2-3 weeks. This is repeated once or twice until sufficient plugging of the canaliculus is achieved to reduce outflow to a specific degree for that individual patient just short of overflow. Once these sizes are established for the lower canaliculus, this composite of plugs are left in for the extended duration until they dissipate or dissolve in 5-6 months. This composite or total length customized plug is then used to insert into the lower canaliculus in each subsequent occlusion therapy session required by the patient. For the upper canaliculus, the same sized plug used initially is also replaced to maintain optimum tear retention. This now customized degree of occlusion is utilized in subsequent extended periods of about 5-6 months for relief of symptoms of dry eye syndrome and for permitting contact lens use by the patient.

A plug for occluding a canaliculus comprises a cylindrical body member having a first outer diameter. The cylindrical body member is provided along an external surface with at least one outwardly extending projection having a second outer diameter greater than the first outer diameter and larger than an inner diameter of an ocular canaliculus Preferably the first outer diameter of the plug is less than and approximately equal to the inner diameter of the ocular canaliculus or lacrimal duct.

The projection preferably takes the form of an annular rib. Where the plug has an extended length, multiple annular ribs may be axially staggered along an external surface of the plug. The ribs are typically coaxial with an axis of the cylindrical body member.

In a preferred embodiment, the annular rib has a smoothly arcuate outer surface, that is, without points or sharp edges. The rib has, for instance, a substantially semi-circular cross-section or partially circular outer perimeter.

The cylindrical body of the plug may be provided on at least one end with a formation taken from the group of a recess and an additional projection extending axially from the cylindrical body member. The recess or projection mates with a projection or recess on an end of another canalicular plug to thereby prevent relative rotation of the two plugs once they are properly deployed in a canaliculus (usually a lower duct) of a patient.

The recess may be a slot and the additional projection a geometrically similar planar or plate-shaped extension of the cylindrical body member.

A kit for use in treating dry eye syndrome comprising a container and a plurality of plugs disposed in the container, each of the plugs having a cross-section accommodating insertion of the respective plug in a canaliculus of a human patient. At least one of the plugs has a first length, at least a second one of the plugs has a second length a first fraction of the first length, and at least a third one of the plugs has a third length a second fraction of the first length. The second and third plugs may have the same length, for instance, a third or a quarter of the length of the first plug. The second and third plugs may be of different lengths, for instance, one a half and the other a quarter of the length of the first plug.

The plugs are titrating or customizing plugs of staggered sizes selected for a step wise customization process wherein the total length of several plugs placed in a canaliculus (typically the lower of the two ducts for a given eye) is incrementally increased over a period of several weeks to determine an optimal plug length for the patient. At the end of the titrating or customizing period, the customization or testing plugs disposed in the canaliculus at that point are left in the canaliculus until they dissipate or dissolve over an extended wear period of 5-6 months. The composite length, i.e., the sum of the lengths of the titrating segments, is noted and, once the original set of plugs effectively dissolve or dissipate, a plug of like size is selected from the kit and is inserted into the lower canaliculus to continue the occlusion process and thereby increase the tear margin of that eye for a netted extended period or for so long as the patient desires this form of therapy for their dry eye symptoms or contact lens wearing option.

The kit may include an extended wear canalicular plug of predetermined dimensions for completely occluding the upper canaliculus of the eye being treated. The kit may further include a set of second extended-wear canalicular plugs of different lengths each equal to a composite length of a respective set of the titrating or calibration plugs. One of the second extended-wear canalicular plugs is selected for insertion into the lower canaliculus upon determination of an optimal length for treating dry eye symptoms without inducing epiphora. As mentioned above, the second extended-wear canalicular plugs are inserted into the lower canaliculus upon dissolution or dissipation of previously inserted plugs.

Each of the plugs in the kit typically includes a cylindrical body member having a first outer diameter preferably less than and approximately equal to an inner diameter of an ocular canaliculus or lacrimal duct. The cylindrical body member is provided along an external surface with at least one outwardly extending projection having a second outer diameter greater than the first outer diameter and larger than the inner diameter of the canaliculus.

The projection preferably but not necessarily takes the form of an annular rib. The rib may be one of a plurality of annular ribs positioned in a staggered locations along an external surface of the cylindrical body member, all of the annular ribs being coaxial with an axis of the cylindrical body member. Any given rib preferably has a smoothly arcuate outer surface, no points or edges, for instance, where the rib has a substantially semi-circular cross-section.

Each of the plugs in the kit may be provided on at least one end with a formation taken from the group of a recess and an additional projection extending axially from the respective cylindrical body member. The recess is exemplarily a slot and the additional projection a planar or plate-shaped extension of the respective cylindrical body member. The slot or recess mates with a formation on another plug or on a deployment tool. In the former case the mating formations prevent undue relative rotation between adjacent plug elements, while in the latter case the mating formations enable or facilitate deployment operations via use of the tool.

Thus, the kit may include an insertion tool configured for rotating a deployed plug that is disposed in an ocular canaliculus. The tool includes a distal tip with a geometric configuration that is rotatively lockable for the deployed plug.

A method for treating dry eye syndrome comprises inserting a first canalicular plug into an upper canaliculus of a patient's eye, the first canalicular plug having a first length. The method further comprises carrying out a testing or calibration process to determine an optimal length of a second canalicular plug for a lower canaliculus of the patient's eye. The titrating or customizing process includes inserting a first test or titrating plug into a lower canaliculus of the patient's eye, the first titrating or customizing plug having a second length, and after a first testing period of predetermined duration during which tear accumulation in the patient's eye is monitored, inserting a second titrating or calibration plug into the lower canaliculus of the patient's eye and adjacent the first test or customizing plug. The second titrating or calibration plug has a third length that is a fraction of the second length. The method optionally includes inserting additional titrating or customizing plugs of respective lengths less than the second length and monitoring eye moisture. Upon a determination that tear accumulation in the patient's eye is satisfactory, all inserted titrating or customizing plugs are kept in the lower canaliculus of the patient's eye and thereafter, after the titrating plugs have dissolved, a new plug with a composite length equal to the combined lengths of the inserted titrating plugs is subsequently inserted into the lower canaliculus of the patient's eye. Thus, the optimal length is a total length that is at least approximately equal to a sum of the lengths of a set of the titrating or customizing plugs actually inserted into the lower canaliculus of the patent's eye.

While it may be the case that the optimal length of the second canalicular plug is equal to the combined lengths of all the titrating or customizing plugs that were inserted into the lower canaliculus during the titrating or customizing procedure, in some cases, if epiphora is induced upon insertion of the last test or calibration plug, then the composite length of all the inserted test or calibration plugs is too great and a shorter length is required for the second or subsequent length of choice to be inserted into the canaliculus.

The inserting of the second titrating or customizing may include rotatively locking the second test or calibration plug and the first test or calibration plug to one another by engaging cooperating elements on adjacent ends of the first test or calibration plug and the second test or calibration plug with one another.

The inserting of any given canalicular plug into a canaliculus of a patient's eye may include both translating the plug along the respective canalicular canal and rotating the plug. The method may be carried out by using a tool where the rotation is causally linked to the translation, for instance, where the tool includes a pair of coaxial tubes, one having a spiral camming slot and the other a lug that is slidably seated in the slot.

BRIEF DESCRIPTION OF THE DRAWINGS

FIG. 1 is a schematic side elevational view of a canalicular plug for deployment in the canaliculus of a patient suffering dry eye syndrome.

FIG. 2 is a schematic right side elevational view of the canalicular plug of FIG. 1.

FIG. 3 is a schematic left side elevational view of the canalicular plug of FIG. 1.

FIG. 4 is a schematic longitudinal cross-sectional view taken along line IV-IV in FIG. 2.

FIG. 5 is a schematic side elevational view of a smaller or shorter canalicular plug for deployment in a canaliculus of a patient suffering dry eye syndrome, for use in a titrating or customizing process to determine an optimal plug size.

FIG. 6 a schematic longitudinal cross-sectional view taken parallel to the plane of the drawing in FIG. 5.

FIG. 7 is a schematic side elevational view of an even smaller or shorter canalicular plug for deployment in a canaliculus of a patient suffering dry eye syndrome, for use in a titrating or customizing process to determine an optimal plug size.

FIG. 8 a schematic longitudinal cross-sectional view taken parallel to the plane of the drawing in FIG. 7.

DETAILED DESCRIPTION

Figure 9:
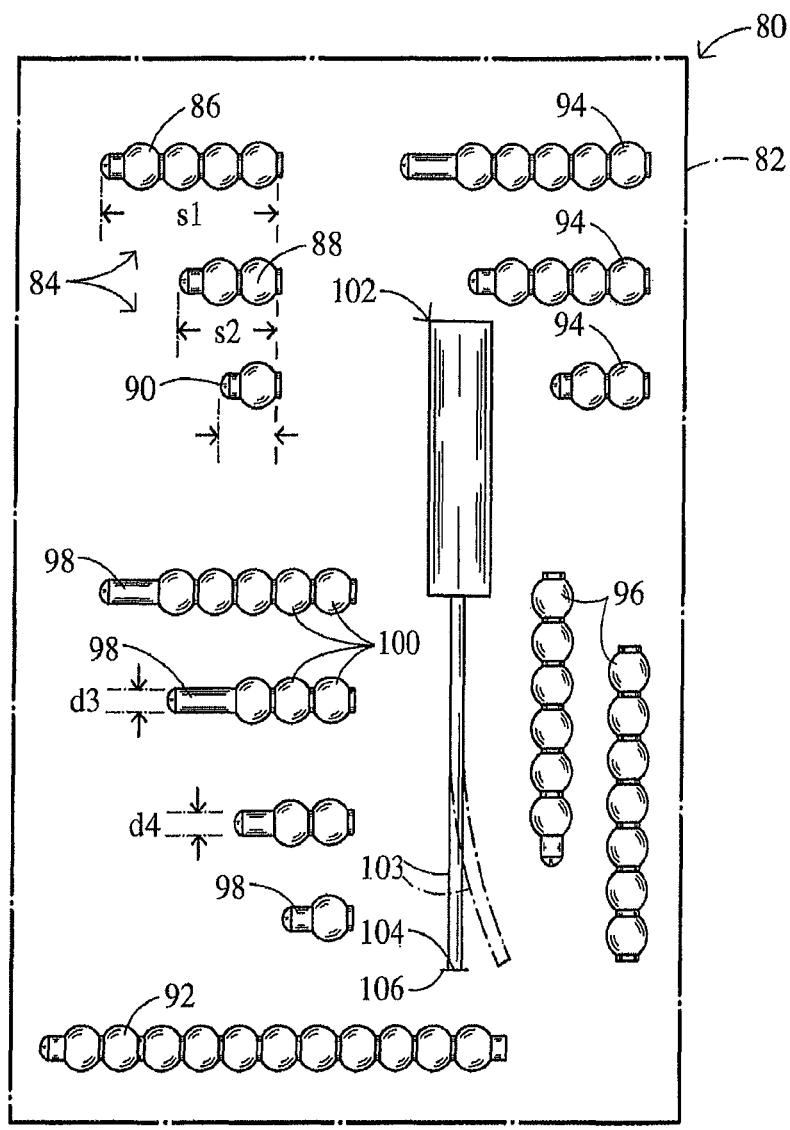
FIG. 9 is a schematic representation of a kit for treating dry eye symptoms.

As illustrated in FIGS. 1-4, a plug 20 for occluding a canaliculus comprises a cylindrical body member 22 having a first outer diameter d1. Cylindrical body member 22 is provided along a cylindrical external or outer surface 24 with at least one outwardly extending projection 26 unitary with body member 22 and having a second outer diameter d2 that is greater than diameter d1 and larger than an inner diameter of an ocular canaliculus. Preferably outer diameter d1 is less than and approximately equal to the inner diameter of the ocular canaliculus or canalicular duct.

Canalicular plug 20 may serve as a long-term or extended-wear plug, which once implanted remains in the canaliculus for months at a time. In that case plug 20 may be longer, with three or more outwardly extending projections 26 spaced from one another and flanked by sections of cylindrical external or outer surface 24 (see also plugs 84 in FIG. 9). Alternatively, plug 20 may serve as a titrating or customizing plug for use in a method to determine an optimal length of an extended wear canalicular plug. Typically, an upper canaliculus of a patient is fitted with a standard size long-term plug (or one of a plurality of standard size plugs) that substantially completely occludes the upper canaliculus, while a testing or calibration process is used on the associated lower canaliculus to determine a plug length that effectively reduces dry eye symptoms but does not lead to epiphora.

Projection 26 preferably takes the form of an annular rib having a smoothly arcuate outer surface, that is, without points or sharp edges. Rib 26 has, for instance, a cross-section with an outer boundary that is a section of a circle. Where plug 20 has an extended length, multiple annular ribs 26 may be axially staggered along external surface 24 of the plug. Ribs 26 are typically coaxial with an axis 28 of cylindrical body member 22.

Cylindrical body member 22 of plug 20 may be provided on at least one end with a formation facilitating insertion of the plug into a canaliculus. If the plug is a test or calibration plug, the formation also serves to rotationally lock the plug to an adjacent plug during the testing process. As illustrated in FIGS. 1-4, a test or calibration plug 20 may include a first formation in the form of a slot-shaped recess 30 at one end and a second formation in the form of a plate-shaped projection 32 at an opposite end. Recess 30 and projection 32 are symmetric about axis 28 and modularly sized: projection 32 is slightly smaller than recess 30 and geometrically similar thereto so that a projection 32 on one canalicular plug of a set of plugs can insert into the recess 30 of another plug. Recesses 30 and projections 32 thus mate with one another to thereby prevent relative rotation of two adjacent plugs once the same are properly deployed in a canaliculus (usually a lower duct) of a patient, typically in a testing or calibration process.

As illustrated in FIGS. 5 and 6, an intermediately sized plug 40 for partially occluding a lacrimal duct or canaliculus in a testing or measurement process together with one or more additional test or calibration plugs comprises a cylindrical body member 42 having a first outer diameter d1'. Cylindrical body member 42 is provided along an external surface 44 with two outwardly extending projections 46a and 46b each having a second outer diameter d2' that is greater than diameter d1' and larger than an inner diameter of an ocular canaliculus or lacrimal duct. Preferably outer diameter d1' is less than and approximately equal to the inner diameter of the ocular canaliculus or lacrimal duct (typically a lower canaliculus) being fitted for a long-term plug.

Projections 46a and 46b are preferably each in the form of an annular rib having a smoothly arcuate outer surface, that is, without points or sharp edges at least along the outermost regions that come into contact with the inner surface of the canaliculus. Ribs 46a has, for instance, a cross-section with an outer boundary that is a section of a circle. Rib 46b is truncated. While rib 46b has a sharp terminal edge 47, the edge preferably has a diameter sufficiently smaller than diameter d2' to avoid undue irritation of the lacrimal duct. Alternatively, edge 47 may be blunted or rounded during the manufacturing process. Ribs 46a and 46b are coaxial with an axis 48 of cylindrical body member 42.

Cylindrical body member 42 of plug 40 is provided on one end with a first formation in the form of a slot-shaped recess 50 and on an opposite end with a second formation in the form of a plate-shaped projection 52. Recess 50 and projection 52 are symmetric about axis 48 and modularly sized: projection 52 is slightly smaller than recess 30 and geometrically similar thereto so that projection 52 can insert into recess 30 of a prior inserted test plug 20. Alternatively, projection 32 may face outwardly upon a seating of test plug 20 in a patient's canaliculus and be received in slot 50 of a subsequently inserted test plug 40. Recesses 30, 50 and projections 32, 52 are thus modularly designed to mate with one another to thereby prevent relative rotation of two adjacent test or calibration plugs 20, 40 once the same are properly deployed in a canaliculus (usually a lower duct) of a patient, typically in a testing or calibration process. This rotational locking serves in part to prevent drifting of the separate titrating or calibration plugs during the testing period and also during an extended wear period thereafter.

Canalicular plug 40 serves as a testing or calibration plug for use together with other titrating plugs such as test or calibration plug 20 in a method to determine an optimal length of a long-term or extended wear canalicular plug typically for a lower canaliculus of a patient. Typically, in such a method outer diameters d1' and d2' of plug 40 are respectively equal to outer diameters d1 and d2 of plug 20. Canalicular test plug 20 is inserted into the lower canaliculus of a patient, before or after the insertion of a longer plug (with a greater number of annular ribs 26) into the associated upper canaliculus. The patient wears the two plugs for a predetermined period of time, typically two or three weeks, and then provides a report on the effectiveness of the occlusion of the canaliculi. If the dry eye symptoms persist, test or calibration plug 40 is then inserted into the lower canaliculus of the patient adjacent plug 20 with projection 52 of plug 40 inserted into recess 30 of plug 20. During a subsequent monitoring period of pre-established duration, typically two to three weeks, the patient wears the two plugs 20 and 40 in the lower canaliculus and thereafter reports on eye dryness to the doctor. If the dry eye symptoms are obviated, without epiphora, then the test plugs 20 and 40 are typically retained in the lower canaliculus for an extended-wear period of up to 5-6 months. In subsequent treatments, single extended-wear plugs are inserted into the lower canaliculus, where the extended-wear plugs have a length equal to the sum of the lengths of the plugs 20, 40 that remain in the patient after the test period. If the test or calibration phase ends with the patient experiencing epiphora, then the subsequent extended-wear plugs selected may have a length somewhat shorter than the combined lengths of the inserted or deployed test plugs.

Although not necessary or advisable, the titrating or test plugs may be removed at the end of the test or calibration phase and the patient provided in the lower canaliculus with a long-term plug of a length about equal to the combined lengths of the test plugs 20 and 40. If the dry eye symptoms persist with plugs 20 and 40 disposed in the lower canaliculus, another test or calibration plug 60 (FIGS. 7 and 8) may then be inserted into the lower canaliculus of the patient over plugs 20 and 40 so that the test plugs 60 and 40 are adjacent to one another.

As illustrated in FIGS. 7 and 8, test plug 60 comprises a cylindrical body member 62 having a first outer diameter d1'. Cylindrical body member 62 is provided along an external surface 64 with one outwardly extending projection 66 having a second outer diameter d2' that is greater than diameter d1' and larger than an inner diameter of an ocular canaliculus. Preferably outer diameter d1' is less than and approximately equal to the inner diameter of the ocular canaliculus (typically a lower canaliculus) being fitted for a long-term plug.

Projection 66 is preferably an annular rib having a smoothly arcuate outer surface, that is, without points or sharp edges at least along the outermost regions that come into contact with the inner surface of the canaliculus. Rib 66 has, for instance, a cross-section with an outer boundary that is a section of a circle. Rib 66 is coaxial with an axis 68 of cylindrical body member 62.

Cylindrical body member 62 of plug 60 is provided on one end with a first formation in the form of a slot-shaped recess 70 and on an opposite end with a second formation in the form of a plate-shaped projection 72. Recess 70 and projection 72 are symmetric about axis 68 and modularly sized: projection 72 has a size and shape selected to enable insertion of projection 72 into recess 30 or 50 of a prior inserted test plug 20 or 40. Alternatively, if projection 32 or 52 faces outwardly upon a seating of test plug 20 or 40 in a patient's canaliculus, projection 32 or 52 is received in slot 70 of subsequently inserted test plug 70. Thus, all recesses 30, 50, 70 and projections 32, 52, 72 are modularly adapted to mate with one another, which serves in part to prevent relative rotation of two adjacent test or calibration plugs 20, 40, 60 once the same are properly deployed in a canaliculus (usually a lower duct) of a patient, typically in a testing or calibration process. The rotational locking serves to hold the test or calibration plugs 20, 40, 60 in place relative to one another.

In summary, a method for treating dry eye syndrome contemplates the insertion of a long-term or extended-wear plug in one canaliculus (usually an upper) and the fitting of the other canaliculus (lower, usually) by testing the effectiveness of a series of test plug sets each having a respective combined or total plug length. In a typical procedure, the lower canaliculus of a patient is fitted with a series of test plug sets each incrementally longer than a prior test plug set. Should any particular set of deployed test plugs result in continued dry eye symptoms, then any long-term or extended-wear plug selected for the patient will be longer than the total plug length of the particular test set. Should any particular set of test plugs result in undue epiphora, then long-term or extended-wear plugs selected for the patient may be shorter than the total length of the test plugs of that test set.

As depicted in FIG. 9, a kit 80 for use in treating dry eye syndrome comprises a container 82 and a plurality of plugs 84 disposed in the container, each of the plugs having a cross-section accommodating insertion of the respective plug in a canaliculus of a human patient. Plugs 84 are independently and individually deployable unitary rigid units of predetermined fixed shape and dimensions. At least one plug 86 in the kit has a first length s1, at least a second plug 88 has a second length s2 which is a fraction of the first length s1, and at least a third plug 90 has a third length s3 which is a different fraction of the first length s1. The second and third plugs 88 and 90 may have a common length (s2=s3), for instance, a third or a quarter of the length s1 of the first plug 86. Preferably, the second and third plugs 88 and 90 are of different lengths, for instance, one a half and the other a quarter of the length s of the first plug 86. As described above, plugs 86, 88, and 90 are test or calibration plugs of staggered sizes adapted for a step wise titration or customization process wherein the total length of several plugs placed in a canaliculus (typically the lower of the two ducts for a given eye) is incrementally increased over a period of several weeks to a few months to determine an optimal plug length for the patient. At the end of the testing or calibration period, the final set of customization or testing plugs is typically allowed to remain in the patient's lower canaliculus and subsequently, after dissolution of the test plugs, a long-term plug is inserted having a length equal to the sum of the lengths of the test plugs determined as optimal for treating dry eye symptoms of the patient. The long-term plug may be cut from a plug blank 92 that has a predetermined standard maximum length. Preferably, kit 80 includes a set of long-term canalicular plugs 94 of different predetermined lengths each equal to a composite length of a respective set of the test or calibration plugs 84. One of the long-wear canalicular plugs 94 is selected for insertion into the lower canaliculus after determination of an optimal length for treating dry eye symptoms without inducing epiphora.

Kit 80 may additionally include one or more long-wear canalicular plugs 96 of predetermined dimensions for completely occluding the upper canaliculus of the eye being treated. Typically, plugs 96 have a length sufficiently large to ensure complete occlusion of the upper canaliculus.

Kit 80 may further include one or more additional sets of test or calibration plugs 98 of staggered lengths which have a larger base diameter d3, annular sealing rings or projections 100 of larger outer diameters d4, and a different selection of lengths.

Each of the plugs 86, 88, 90, 92, 94, 96, 98 in kit 80 includes, as discussed above with reference to FIGS. 1-8, a cylindrical body member having a base outer diameter less than and approximately equal to an inner diameter of an ocular canaliculus. Each plug 86, 88, 90, 92, 94, 96, 98 is formed along an external surface of the respective cylindrical body member with at least one outwardly extending preferably annular projection having an outer diameter greater than the base diameter of the cylindrical body member and larger than the inner diameter of the canaliculus. As discussed above, the projections preferably but not necessarily take the form of annular ribs.

Figure 10:
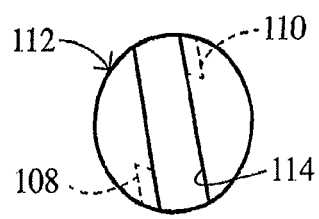
FIG. 10 is a diagrammatic partial end elevational view, on an enlarged scale, of an ocular plug with a slot and undercuts for facilitating insertion.

Each of the test or calibration plugs 86, 88, 90, 98 in the kit 80 may be provided on each end with a recess (e.g., slot) or an axial projection (e.g., tongue or plate), while each of the long-term plugs, 92, 94, 96 might bear such a formation on only one end, that is, the outer end, for facilitating insertion and optional removal procedures. The recesses and projections on the test or calibration plugs 86, 88, 90, 98 mate with complementary formations on other test or calibration plugs 86, 88, 90, 98, preventing or reducing undue relative rotation between adjacent plug elements. The end formations on the long-term plugs, 92, 94, 96 cooperate with a deployment tool 102 for facilitating insertion and optional retraction procedures. Tool 102 is configured for rotating a deployed plug (test or long-term) that is disposed in an ocular canaliculus. Tool 102 includes a flexible shaft 103 and a distal tip 104 with a geometric configuration that is rotatively lockable to and removable from the deployed plug. Tool tip 104 may include one or more fingers or nubs 106 that are alternately insertable into and removal from respective undercuts 108 and 110 (FIG. 10) in an ocular plug 112. Undercuts 108 and 100 communicate with a slot 114 that receive the tip 104 of tool 102. Fingers or nubs 106 and undercuts 108 and 110 enable the application of a tensile force on the canalicular plugs, so that the plugs are entrained to the tool and more easily extractible from a canaliculus. It is to be noted that the removal of plugs is likely rare and carried out only under unusual circumstances.

A method for treating dry eye syndrome utilizing kit 80 comprises inserting a selected long-term canalicular plug 96 into an upper canaliculus of a patient's eye. The method further comprises carrying out a titrating or calibration process to determine an optimal length of a long-term canalicular plug for a lower canaliculus of the patient's eye. The testing or calibration process includes inserting a first test or calibration plug 86, 88, or 90 or one of plugs 98 into the lower canaliculus of the patient's eye. Thereafter, the patient wears long-term plug 96 and the first test plug 86, 88, 90, 98 during a first testing period of predetermined duration, typically a two to three weeks, during which the patient monitors tear accumulation in his or her eye. If necessary, that is, if dry eye symptoms persist, a second test or calibration plug 86, 88, 90, 98 is inserted into the lower canaliculus of the patient's eye and adjacent or over the first test or calibration plug 86, 88, 90, 98. The second test or calibration plug typically has length that is a fraction of the length of the first test or calibration plug. (However, a set of modular calibration plugs of the same length may be used in the titrating or fitting process.) The patient then monitors eye moisture for another period of typically two to three weeks. Upon a determination that tear accumulation in the patient's eye is satisfactory, the inserted test or calibration plugs 86, 88, 90, 98 are allowed to remain in the patient's canaliculus for an extended period of up to 5 or 6 months. Alternatively, but typically unnecessary, the test or calibration plugs are removed from the lower canaliculus of the patient's eye and replaced with a final canalicular plug cut from blank 92 or selected from plugs 94, this final canalicular plug having a length that is at least approximately equal to a sum of the lengths of the test or calibration plugs 86, 88, 90, 98 that provided a satisfactory or optimal correction of the patient's dry eye symptoms.

In general, it is contemplated that the fitting of one canaliculus of an upper and lower pair is achieved by a series of test plug sets. A long-term plug has a length selected in accordance with the results of the test plug sets. If dry eye symptoms persist with any one test plug set, then the length of any long-term plug for the patient will be longer than the combined lengths of that test plug set. Conversely, if epiphora results with any selected test plug set, then the length of any long-term or extended-wear plug will be shorter than the combined lengths of that selected test plug set. It is possible to select a length of a long-term plug on the basis of an interpolation where one test plug set results in dry eye symptoms and a next-longer test plug set results in epiphora.

The inserting of the long-term and calibration plugs and the removing of the calibration or fitting plugs may be implemented by rotating the plugs during the exertion of a pushing or pulling force on the plugs.

The canalicular plugs described herein comprise hydrophilic and biodegradable materials known in the medical industry. Examples include aliphatic polyesters such as polyglycolic acid (PGA), polylactic acid (PLA), Poly ε-caprolactone (PCL), etc.; polyaminoacids, and co-polymers of polyamino acids.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for treating dry eye syndrome, comprising: (a) inserting a first canalicular plug into an upper canaliculus of a patient's eye, said first canalicular plug having a first length; (b) carrying out a testing or calibration process to determine an optimal length of a second canalicular plug for a lower canaliculus of the patient's eye, said testing or calibration process including (i) inserting a first test or calibration plug into a lower canaliculus of the patient's eye, said first test or calibration plug having a second length, (ii) after a first testing period of predetermined duration during which tear accumulation in the patient's eye is monitored, inserting a second test or calibration plug into the lower canaliculus of the patient's eye and adjacent said first test or calibration plug, (iii) optionally repeating steps (i) and (ii) using additional test or calibration plugs of respective lengths, and (c) thereafter inserting a long-term or extended-wear canalicular plug of said optimal length into the lower canaliculus of the patient's eye, said optimal length being a total length that is at least approximately equal to a sum of the lengths of a set of the test or calibration plugs disposed in the lower canaliculus of the patient's eye upon termination of said testing or calibration process.

2. The method defined in claim 1 wherein the inserting of said second test or calibration plug includes rotatively locking said second test or calibration plug and said first test or calibration plug to one another by engaging cooperating elements on adjacent ends of said first test or calibration plug and said second test or calibration plug with one another.

3. The method defined in claim 1 wherein the inserting of any one of the first and second canalicular plug into a canaliculus of a patient's eye includes rotating the first or second canalicular plug respectively.

4. The method defined in claim 1 wherein said second test or calibration plug has a third length that is a fraction of said second length.

5. A method for treating dry eye syndrome, comprising: (a) inserting a first canalicular plug into an upper canaliculus of a patient's eye, said first canalicular plug having a first length; (b) carrying out a testing or calibration process to determine an optimal length of a second canalicular plug for a lower canaliculus of the patient's eye, said testing or calibration process including (i) test or calibration plugs into a lower canaliculus of the patient's eye, said test or calibration plugs having respective lengths and (ii) monitoring tear accumulation in the patient's eye in response to different cumulative lengths of said test or calibration plugs, and (c) thereafter inserting a long-term or extended-wear canalicular plug of said optimal length into the lower canaliculus of the patient's eye, said optimal length being a total length that is at least approximately equal to a sum of the lengths of a set of the test or calibration plugs disposed in the lower canaliculus of the patient's eye upon termination of said testing or calibration process.

6. The method defined in claim 5 wherein the inserting of said test or calibration plugs includes rotatively locking at least two of said test or calibration plugs to one another by engaging cooperating elements on adjacent ends of said at least two of said test or calibration plugs with one another.

7. The method defined in claim 5 wherein the inserting of any one of the first and second canalicular plug into a canaliculus of a patient's eye includes rotating the first or second canalicular plug respectively.

8. The method defined in claim 5 wherein said test or calibration plugs have different lengths.

\* \* \* \* \*